United States Patent [19]
Hendricks

[11] Patent Number: 5,699,789
[45] Date of Patent: Dec. 23, 1997

[54] DRY POWDER INHALER

[76] Inventor: Mark R. Hendricks, 515 Wild Oak Dr., Manitowoc, Wis. 54220

[21] Appl. No.: 613,413
[22] Filed: Mar. 11, 1996
[51] Int. Cl.$^6$ ................................................. A61M 15/00
[52] U.S. Cl. ................................. 128/203.15; 604/58
[58] Field of Search .......................... 604/58, 48, 73; 128/203.15, 203.21, 203.24

[56] References Cited

U.S. PATENT DOCUMENTS

| | | | |
|---|---|---|---|
| 631,621 | 8/1899 | Curran | 128/203.15 |
| 2,598,365 | 5/1952 | Dunfresne | 128/200 |
| 4,353,365 | 10/1982 | Hallworth et al. | 128/203.15 |
| 4,570,630 | 2/1986 | Elliot et al. | 128/203.15 |
| 4,739,754 | 4/1988 | Shaner | 128/203.15 |
| 4,852,561 | 8/1989 | Sperry | 128/200.23 |
| 5,113,855 | 5/1992 | Newhouse | 128/203.12 |
| 5,161,524 | 11/1992 | Evans | 128/203.15 |
| 5,202,110 | 4/1993 | Dalby et al. | 424/45 |
| 5,239,993 | 8/1993 | Evans | 128/203.15 |
| 5,254,330 | 10/1993 | Ganderton et al. | 428/46 |
| 5,295,479 | 3/1994 | Lankinen | 128/203.15 |
| 5,320,094 | 6/1994 | Laube et al. | 128/203.12 |
| 5,320,714 | 6/1994 | Brendel | 128/203.15 |
| 5,327,883 | 7/1994 | Williams et al. | 128/203.12 |
| 5,341,801 | 8/1994 | Zechner | 128/203.15 |
| 5,347,999 | 9/1994 | Poss et al. | 128/203.15 |
| 5,349,947 | 9/1994 | Newhouse et al. | 128/203.21 |
| 5,372,128 | 12/1994 | Haber et al. | 128/203.21 |
| 5,376,386 | 12/1994 | Ganderton et al. | 424/499 |
| 5,388,572 | 2/1995 | Mulhauser et al. | 128/203.15 |
| 5,388,573 | 2/1995 | Mulhauser et al. | 128/203.15 |
| 5,435,301 | 7/1995 | Herold et al. | 128/203.15 |
| 5,437,271 | 8/1995 | Hodson et al. | 128/203.15 |
| 5,533,505 | 7/1996 | Källstrend et al. | 128/203.15 |
| 5,568,807 | 10/1996 | Mecikalski | 128/203.15 X |

OTHER PUBLICATIONS

Fong et al., "Inhalation Devices for Asthma", *Canadian Family Physician* 39:2377 (Nov. 1993).
Persson et al., "A New Multiple Dose Powder Inhaler, (Turbuhaler®) . . . ", *Eur. Respir. J.* 1:681–684 (1988).
Carpi, J., "Drug Companies Try to Kick CFC Habit," *Internal Medicine News*, p. 24 (Jun. 15, 1993).

*Primary Examiner*—Michael Powell Buiz
*Assistant Examiner*—N. Kent Gring
*Attorney, Agent, or Firm*—Godfrey & Kahn, S.C.

[57] ABSTRACT

The present invention is a dry powder inhaler that is operable to deliver a dry powder medication to the lungs of a patient without the use of a propellant. The inhaler device is a tubular shell with an opening at either end of the shell and an air passageway therethrough, a medication storage chamber, an axially moved air inlet closure member covering the air inlet opening(s), and a slidable medication dosing tray attached to the closure member. In use, the air inlet closure member is pulled in a direction away from the user while the patient inhales, causing the simultaneous introduction and flow of air through the air passageway, and dispersement of a dosage of the medication into the air passageway. The patient then inhales the air/medication mix which passes into the lungs.

15 Claims, 3 Drawing Sheets

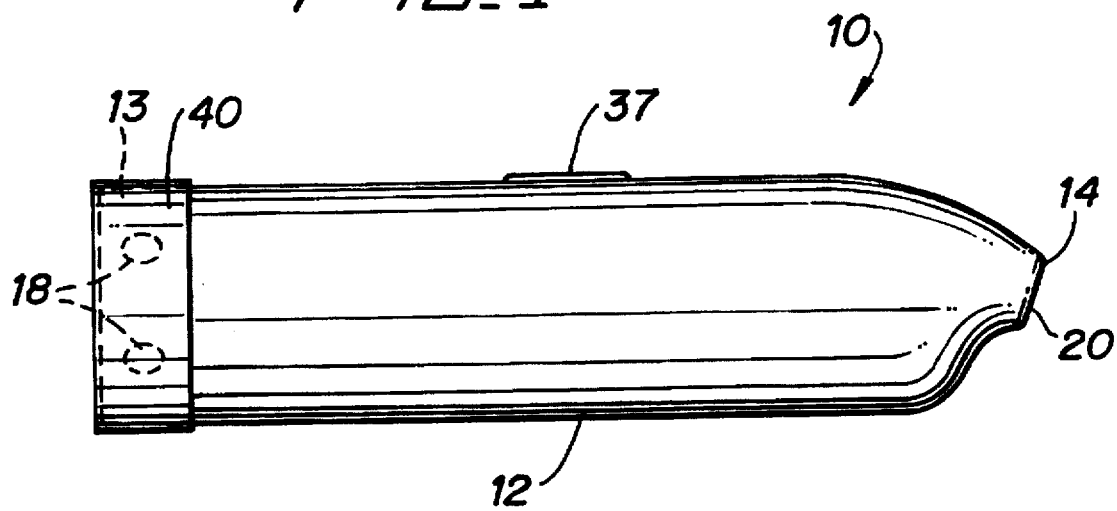
FIG_1
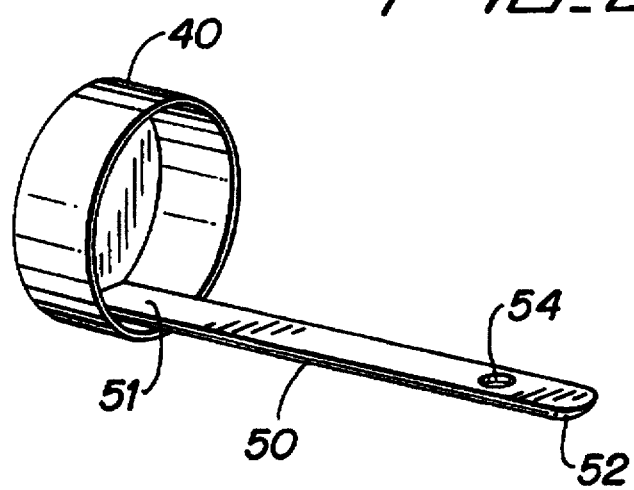
FIG_2

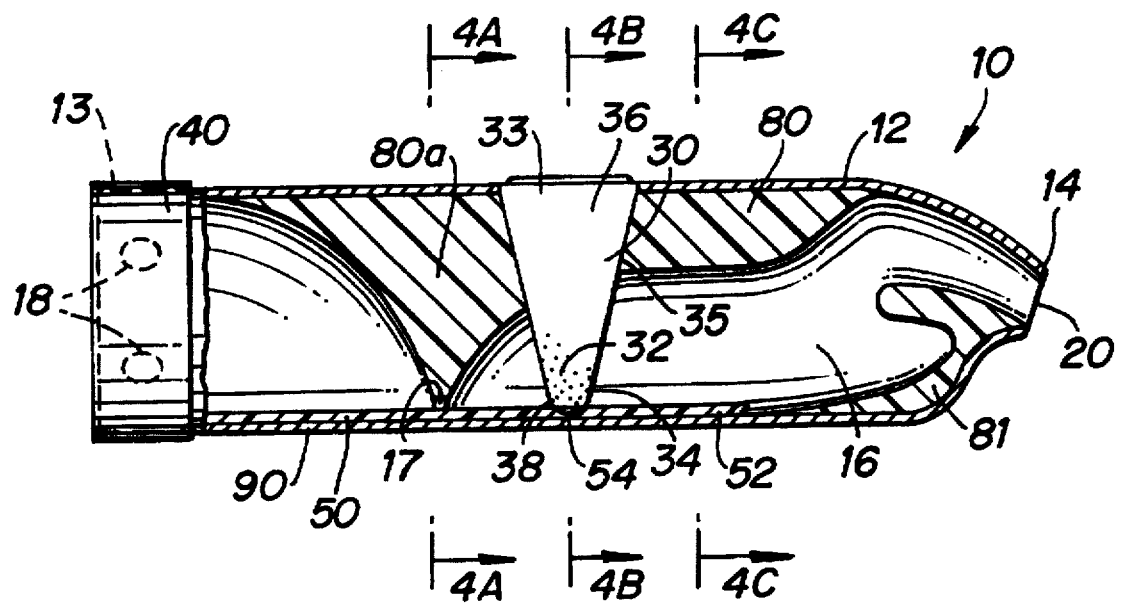
FIG_3
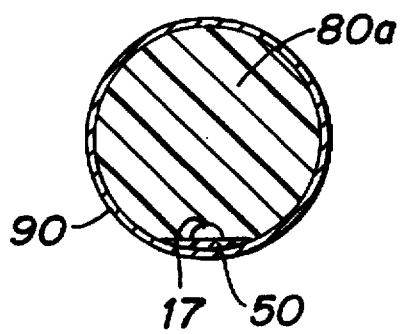
FIG_4A
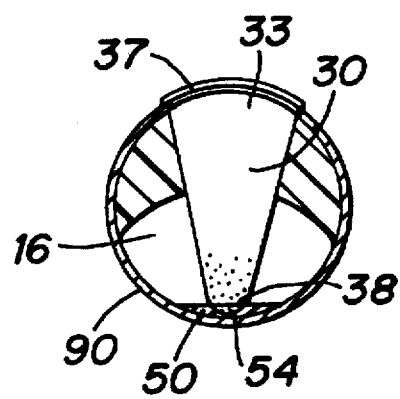
FIG_4B

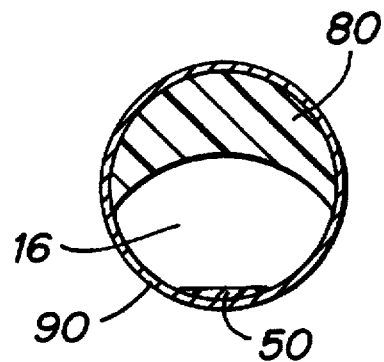
FIG_4C
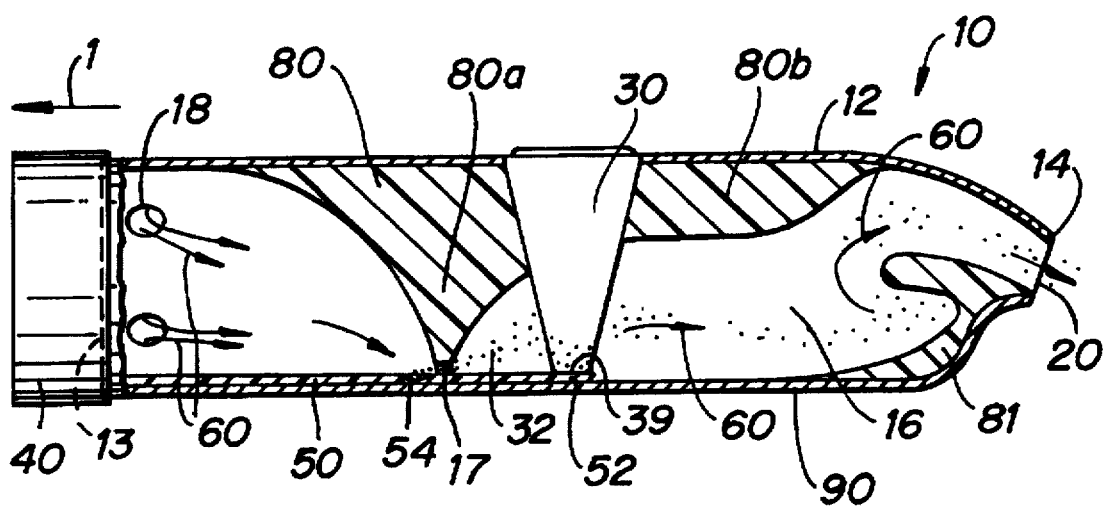
FIG_5

DRY POWDER INHALER

BACKGROUND OF THE INVENTION

There are several devices available for delivering aerosol medication to patients. One type is a neubulizer which comes in the form of a venturi-jet type or ultrasonic piezoelectric type, and produces an aerosol from a liquid drug solution. Drawbacks of nebulizers include a lack of portability, the inconvenience of having to load each dose individually into the device, and the time required to inhale each dose. Nebulizers account for fewer than 1% of the drug delivery devices used by patients.

Another type of delivery device is a metered dose inhaler (MDI) which is composed of a chlorofluorocarbon propellant such as freon in a pressurized canister. MDIs have been the mainstay drug delivery device for medications used in the treatment of asthma and chronic obstructive lung disease. However, the use of freon is soon to be banned, and FDA approval of a replacement propellant will likely take years and increase costs. Additionally, MDIs are associated with frequent dosing errors related to the need to simultaneously aim the device toward the oropharynx, press down a mechanism to actuate the high-velocity spray, and slowly inhale the medication. Radioisotope studies have shown that only 15% of the medication dose delivered using an MDI is inhaled into the bronchial tubes, with the remainder impacting on the oral mucosa or being exhaled into the environment.

A third type of delivery device is a dry powder inhaler (DPI) which comes in single-dose (Spinhaler™, Rotahaler™) or multi-dose (Turbuhaler™). Dry powder inhalers generally rely on the energy of the patient's own inhalation to draw a dose of medication into the lungs.

A problem with DPIs is that the powdered medication tends to clump, making dosing inconsistent and dispersal of the particles too large for optimal inhalation into the bronchial tubes. For example, U.S. Pat. No. 5,341,801 discloses an inhaler that delivers a dry powder medication into an interior air passageway, and the powder is then inhaled. Particle-to-particle interaction, however, affects the ability of a dry powder medication to redisperse into smaller particles suitable for inhalation. Typically, agglomerated particles of the medication are delivered to the patient, rendering the medication less effective. In addition, particles of a medication have larger forces of inertia, causing them to impact on the oropharynx and subsequently swallowed rather than being inhaled into the bronchial tubes.

Therefore, an object of the invention is to provide a multiple-dose inhaler device for consistently delivering a measured dosage amount of a dry powder medication into the lungs of a patient. Another object is to provide an inhaler that eliminates the possibility of the patient receiving multiple doses. Another object is an inhaler that operates without the use of a propellant. Another object is an inhaler that will deliver a dry powder medication as small and separated particles that are not agglomerated. Yet another object is to provide an inhaler device that is small, compact, and easy to operate by the user.

SUMMARY OF THE INVENTION

These and other objects are achieved by the present invention, which provides a multiple-dose dry powder inhaler for delivering a metered dose of dry powder medication to a patient through inhalation, without the use of propellants. The inhaler is operable to use in treating a patient suffering from a respiratory disease or lung ailment such as asthma, chronic obstructive lung disease, cystic fibrosis, pneumonia, and the like. The inhaler device delivers to a patient a dose amount of medication in particle sizes of about 0.5–5 microns.

The dry powder inhaler is composed of a tubular shell member with a hollowed section therein that functions as an air passageway and terminates in an aperture at either end of the tubular shell member. The aperture at the first end allows air to flow into the air passageway of the tubular shell member, and the aperture at the second end (i.e., mouthpiece) allows air to flow out into the mouth of the user. The air passageway is contoured to direct the flow of air from the air inlet aperture downward past a source of dry powder medication, through a narrowed channel near the center of the inhaler, and then out through the air outlet aperture.

A slidable member that covers the air inlet aperture is attached to the first end of the shell member. This member is operable to move axially to uncover the air inlet which allows air to flow into the air passageway, or cover the air inlet to prevent air flow through the device.

A medication storage chamber is formed in the tubular shell member, preferably about midway between the two ends of the device. The storage chamber has two openings. The first opening extends through the shell for receiving the powdered medication. A cover is provided to seal this opening to contain the medication in the chamber. The second opening is smaller and allows medication to be dispensed from the medication storage chamber onto a slidable dosing tray.

The slidable dosing tray for dispensing the medication from the storage chamber into the air passageway is attached to the air inlet closure member. The slidable dosing tray and the air inlet closure member move as a unit in the device. The slidable dosing tray is generally planar and in the form of a rod or bar, with its second end extending into the shell member in contact with the dispensing aperture of the storage chamber. The second end of the slidable dosing tray includes a metering member, preferably in the form of a depression, that is positioned under the dispensing aperture of the storage chamber when the air inlet is covered. In this position, a dosage amount of the medication is deposited into the depression of the metering member. When the air inlet is uncovered, the powdered medication in the metering member is transferred to the air passageway and becomes mixed with the air flowing through the air passageway. Simultaneously, the dispensing aperture of the storage chamber is sealed by the distal end of the slidable dosing tray to prevent the flow of more than the desired dosage amount of medication into the air passageway.

In use, the patient draws the moveable air inlet closure away from the end of the shell member to expose the air inlet aperture so that air can flow into the air passageway. As the closure member is moved, so too is the slidable dosing tray which simultaneously transfers a single dose of the medication from the metering member into the aerosolization chamber. As the user inhales air through the air outlet of the mouthpiece, the dose of medication transferred to the air passageway becomes mixed with the air. The device includes one or more baffles to direct the air flow through the air passageway past the medication source, and to break up the powder medicament into small particles that are preferably about 0.5–5 microns in size. Upon inhalation, the air/powder mixture passes through the air outlet aperture and into the lungs of the patient.

In use, the dry powder inhaler provides delivery of a dry powder medication to a patient. The inhaler is operated by (i) placing the patient's mouth over the mouthpiece and the air outlet aperture of the dry powder inhaler described herein; (ii) axially moving the air inlet closure member of the device to expose the air inlet aperture which simultaneously moves the slidable dosing tray to dispense the dry powder medicament contained therein into the air passageway; and (iii) inhaling to cause air to flow through the air inlet aperture into the air passageway, to aerosolize the dispensed powder medicament, and to deliver the medicament in particle form into the lungs of the user.

Advantageously, the present dry powder inhaler provides a reproducible dose output of a dry powder medication in which the particles are not agglomerated and of an effective particle size for delivering a major proportion of the dispensed amount of medication into the lungs to effectively treat the ailment of the user. Another advantage of the present inhaler is that it is less expensive to manufacture than an aerosol canister of a metered dose inhaler (MDI). Also, use of the device is non-polluting compared to devices that use freon or other like propellant. The device is also easier to use than an MDI that operates by means of a high velocity jet of propellant or a medication spray. Also, the present device is easier for the user to inhale through compared to other multidose dry powder inhalers (DPIs). The present DPI has less pressure drop at a constant 30 l/minute flow of inhaled volume of air. In addition, the present dry powder inhaler is easier to use than current single dose DPIs because it will provide aerosolization of a powdered medication with a single inhalation (at about 30 l/minute flow) by the user.

BRIEF DESCRIPTION OF THE DRAWINGS

Throughout the following views, reference numerals will be used in the drawings, and like reference numerals will be used throughout the several views in the description to indicate corresponding parts of the invention.

FIG. 1 is a side view of the dry powder inhaler of the invention;

FIG. 2 is a side view of the slidable dosing tray attached to the air inlet closure member.

FIG. 3 is a cross-sectional side view of the inhaler of FIG. 1, shown in the closed position;

FIGS. 4 A–C are cross-sectional views of the inhaler of FIG. 3. FIG. 4A is a view showing the baffle, orifice and dosing tray. FIG. 4B is a view showing the baffle, air channel and depression in the dosing tray. FIG. 4C is a view showing the air channel and baffle.

FIG. 5 is a cross-sectional side view of the inhaler of FIG. 1, shown in the opened position.

DETAILED DESCRIPTION OF THE DRAWINGS

The present invention provides a device for delivering a dry powder medication to a patient by inhalation without the use of a propellant.

Referring now to the drawings, FIGS. 1–5 are illustrations of an embodiment of the dry powder inhaler in accordance with the invention, designated generally by the numeral 10. As shown in FIG. 1, the dry powder inhaler 10 includes a tubular shell member 12 with a first end 13 and a second end 14. At the first end 13 of the tubular shell member 12, there are one or more air inlet apertures 18. Preferably the sum of the aperture area exceeds the cross-sectional area of the tubular shell member 12. This is to assure a sufficient drop in air pressure related to the increased velocity of air flow at the throat 17 in order to aerosolize the dry powder medicament.

At the second end 14 (i.e., mouthpiece) of the tubular shell member 12, there is an air outlet aperture 20. An air passageway 16 extends through the tubular shell member 12 from the air inlet aperture 18 to the air outlet aperture 20. A lid or other cover (not shown) can be placed over the outlet aperture 20 to seal the mouthpiece.

Slidably attached to the first end 13 of the tubular shell member 12 is a closure member 40 that is axially moveable from a closed position wherein the air inlet apertures 18 are covered (FIGS. 1 and 3), to an opened position wherein the air inlet apertures 18 are uncovered (FIG. 5). An axially moveable dispensing tray 50 (i.e., slidable dosing tray) having a first end 51 that is fixedly attached to the closure member 40, and a second end 52 that extends axially inward into the air passageway 16 of the tubular shell member 12. The slidable dosing tray 50 is positioned within the inhaler device 10 such that it is in communication with the inside wall 90 of the shell member 12 and no air flows beneath dosing tray 50.

The dry powder inhaler 10 also includes a chamber 30 adapted for storage and dispensing of a dry powder medicament 32. Chamber 30 extends through tubular shell member 12 into air passageway 16, preferably about midway between the first end 13 and the second end 14 of the inhaler 10. The chamber 30 has a first end 33 with an aperture 36 sized to receive the dry powder medicament 32 that is poured into the chamber 30, and a second end 34 with an aperture 38 that is sized to dispense medicament 32 from the chamber.

As shown in FIGS. 2 and 3, the second end 52 of the dosing tray 50 includes a metering member 54 adapted to receive a metered amount of dry powder medicament 32 that is automatically dispensed from chamber 30 through aperture 38. Preferably, the diameters of the dispensing aperture 38 and metering member 54 are sized such that, when in communication, medicament 32 flows into metering member 54 but not into the air passageway 16.

As shown, metering member 54 is a recessed or spoon-shaped depression that is sized such that, when in communication with the dispensing aperture 38, a metered dosage amount of the medicament 32 is dispensed and maintained therein. The medicament 32 then flows out into air passageway 16 when the slidable dosing tray is moved in the direction of arrow 1 (FIG. 5), and air flowing through the device contacts the medicament 32. As shown in FIG. 3, when the inhaler device 10 is not in use (i.e., in the closed position), the metering member 54 is aligned with the dispensing aperture 38 of the chamber 30, and a portion of the medicament 32 flows through the aperture 38 of the chamber 30 and into the depression of the metering member 54.

In a preferred embodiment of the dry powder inhaler 10, the closure member 40 is similar in cross-sectional dimension to the first end 13 of the tubular shell member 12, and is adapted to fit over the first end 13, as shown in FIG. 3. It will be understood by those skilled in the art that a variety of closure members can be employed within the scope of the present invention to achieve the same purpose. For example, a member large enough to cover the air inlet aperture 18 and which is axially moveable along either the interior or exterior of the tubular shell member 12 can perform the same function.

Referring to FIG. 2, slidable dosing tray 50 is a generally planar, rod-like extension that is attached at its first end 51 to the closure member 40. The closure member 40 and the slidable dosing tray 50 can be fabricated as a unitary piece, for example, by injection molding, or can be made separately and then attached together, for example, by a pin, adhesive, or other like connecting means.

As shown in FIG. 3, an air passageway 16 is formed by means of baffle 80 and extends throughout the tubular shell member 12 between the air inlet 18 and the air outlet 20 at the mouthpiece. Baffle 80 can be one or more pieces, and can be attached to or made as a unitary piece with the inner wall 90 of the shell member 12. In a preferred embodiment, the baffle member 80 is a concave member affixed to the shell member.

Baffle 81 functions to distribute the aerosolized medication evenly over the inhaled volume of air. Baffle 80 is also designed for that purpose to not allow particles of the medication to "settle" and drop to the floor of the inhaler. As illustrated in FIGS. 3, 4A and 5, baffle 80a is configured to form a narrow channel 17 (i.e., throat or orifice) upstream of chamber 30. As shown in FIG. 5, the curvature of baffle 80 directs air to and from the narrow channel portion 17 (i.e., orifice or throat) of the air passageway 16. The orifice 17 is sized so as to greatly increase air velocity thereby decreasing the pressure (i.e., Venturi effect) resulting in suction of the metered dose of powder into the airstream. Orifice 17 and air passageway 16 are further illustrated in a cross-sectional view in FIGS. 4A, 4B and 4C. It is preferred that the size of the orifice 17 is about 0.08 –0.15 in $^2$, preferably about 0.1 in$^2$.

The placement of the medicament chamber 30 or other barrier downstream from the orifice 17 formed by baffle 80a, impacts the larger-sized particles of the medicament (greater than about 20 microns), which causes the particles to break up into smaller particles of less than about 5 microns, which is a size suitable for inhalation into the bronchial tubes of the user. The position of the medication reservoir 30 from the orifice 17 is calculated such that larger particles and/or agglomerated particles will impact against the sides of the reservoir 30 and break up into smaller particles. The smaller particles are "dragged" by the curved airstream around the funnel-shaped medication chamber 30. Preferably, edge portion 39 of end 34 of chamber 30 is positioned about 0.5–1 inch from orifice 17 such that the flow of air/medicament through orifice 17 is at an about 90° angle to maximize the impact of particles on the side of medication chamber 30. With orifice 17 positioned at a distance of about 1-inch, particles greater than about 35μ will impact the chamber 30, and at a distance of about 0.5-inch, particles greater than about 20μ will impact. To provide further means for impacting and breaking up particles of the medicament 32, a rod or other barrier (not shown) can be inserted between orifice 17 and chamber 30.

Baffles or barriers (foils) 80b, 81 placed downstream from chamber 30 function primarily to provide sufficient air flow to prevent settling and evenly distribute the particles of the dry powder throughout the volume of the inhaled air. The barrier member 81 can be formed as a unitary piece with or fixedly attached to the inside wall 90 of the shell member 12 near its second end 14. The curvature of the barrier 81 also functions to break up agglomerated particles of the medicament 32 by causing turbulence in the passing air flow.

The medication chamber 30 is sized to receive and contain multiple doses of the dry powder medication. Preferably, the width of the receiving aperture 36 is greater than the width of the dispensing aperture 38. As shown, the sides 35 of the chamber 30 are generally sloped inward from the periphery of the receiving aperture 36 to that of the dispensing aperture 38 to provide a cone-shaped chamber.

Optionally, a window (not shown) can be incorporated into the tubular shell member 12 adjacent the chamber 30 for viewing the level of medicament 32 so that the patient can determine when to refill the chamber 30.

The dry powder medicament 32 can be poured into chamber 30, and a lid 37 placed over aperture 36 to seal the medicament 32 therein. Medicament 32 can also be introduced into the dry powder inhaler 10 by way of a medication cartridge (not shown) that fits into the chamber 30. Such a cartridge generally has the same shape as the chamber 30 with a dispensing aperture that fits into the chamber 30 proximate the dispensing aperture 38. The dispensing aperture of the cartridge is initially sealed to contain the medicament in the cartridge until use. To insert the cartridge into the chamber 30, the cartridge is held upside-down with dispensing aperture 37 positioned in an upward direction, the seal is removed from the cartridge dispensing aperture and, with the inhaler device 10 being held such that receiving aperture 36 is positioned in an upward direction, the cartridge is inserted and sealed into chamber 30.

Referring to FIG. 5, when the closure member 40 is moved in the direction of arrow 1 to the opened position, member 40 operates to move the slidable dosing tray 50 likewise in the direction of arrow 1. This removes metering member 54 containing a measured dose of medicament 32 from communication with the dispensing aperture 38 of the chamber 30. In this position, the metered dose of medicament 32 is exposed to the air flow in the air passageway 16, shown generally by the arrows 60. Additionally, when in this position, the second end 52 of the slidable dosing tray 50 operates to seal the dispensing aperture 38 of the chamber 30. As the patient inhales air through the air outlet 20, the metered dose of dry powder medicament 32 is mixed with the air in the air passageway 16 and passes through the air outlet 20, and into the lungs of the patient.

In a preferred embodiment, the inhaler is approximately 1 inch wide (w) by about 2–3 inches long (1), and is preferably constructed of a plastic material. The chamber 30 is preferably sized to store about 100–250 doses of the medicament 32 at about 10–800 micrograms plus excipients per dose. Preferably, chamber 30 is constructed, at least partially, of a transparent plastic, and shell member 12 includes a window for viewing chamber 30. This construction allows the patient to view the medicament 32 and determine when to either change the cartridge 31 or refill the chamber 30.

Examples of dry powder medications 32 that can be dispensed from the inhaler include an antibiotic such as aminoglycosides for treating the airways of a patient suffering from a chronic illness such as cystic fibrosis, AIDS, and the like; a sodium channel blocker or other mucolytic agent for lubricating the secretions of a patient with cystic fibrosis; peptide hormones; antiinflammatory steroid drugs such as triamcinolone, flunisolide, and the like; bronchodilator drugs such as albuterol, terbutaline and others; and the like.

Use of the Inhaler

To use the dry powder inhaler 10 to administer a measured dose of dry powder medicament 32 to a patient, chamber 30 is filled with medicament 32 and sealed. In a preferred use, a medication cartridge (not shown) is placed in the chamber 30 after removing a seal covering the dispensing aperture of the cartridge. The cartridge contains multiple doses of the medicament 32 so that the patient does not have to refill the chamber 30 prior to each use.

The patient places his or her mouth over the mouthpiece and air outlet aperture 20 of the tubular shell member 12, and moves the closure member 40 from the closed position to the opened position by pulling the closure member 40 in the direction of arrow 1 (FIG. 5). This causes slidable dosing tray 50 and the metering member 54 (i.e., depression) to move out of communication with the dispensing aperture 38 of the storage chamber 30, and simultaneously seals the storage chamber 30 with the second end 52 of the slidable dosing tray 50. Placing the closure member 40 in the opened position also causes the medicament 32 in the metering member 54 to be dispensed.

The patient then inhales, which causes air to enter the air inlet aperture 18 and flow through the air passageway 16 (arrows 60). The air mixes with the medicament 32 in the depression 54, and the air/medicament mixture passes through the orifice 17. The larger particles of the medicament 32 impinge on the sides of the chamber 30 and break into smaller particles that pass around the funnel-shaped chamber 30.

The medicament 32 is further dispersed by the baffle members 80b and 81 before entering into the mouth of the patient. The closure member 40 is then moved in the opposite direction of arrow 1 to the closed position. This causes the slidable dosing tray 50 to move axially inward into the tubular shell member 12 whereupon the metering member 54 is placed back into communication with the dispensing aperture 38 of the storage chamber 30. Another measured dose of medicament 32 is automatically dispensed into the metering recess 54 and the dry powder inhaler 10 is ready for subsequent use.

Article of Manufacture/Kit

The dry powder inhaler 10 can be constructed and/or packaged as a kit of detachable parts that can be later interconnected together. It is preferred that dry powder inhaler 10 can be disassembled into individual parts to facilitate cleaning. Such a kit can be composed of the following components of the dry powder inhaler 10, either alone or in combination: (i) a tubular shell member 12; (ii) a medication cartridge, or a supply of medicament 32 in a packaging; and (iii) a preassembled closure member 40/slidable dosing tray 50, or separate pieces of those components. The kit can also include instructions for assembly and/or for using the inhaler 10.

To assemble the dry powder inhaler 10, the preassembled closure member 40/slidable dosing tray 50 is attached to the first end 13 of the shell member 12 by inserting the slidable dosing tray 50 into the shell 12. The slidable dosing tray 50 is inserted into the shell 12 so that it is in intimate contact with the inside wall 90 of the shell member 12 such that no air flows beneath dosing tray 50 or the metering member 54. A medication cartridge is then inserted into the medication storage chamber 30 as previously described, or medicament 32 is poured into the chamber 30, and the chamber 30 is sealed by means of lid 37. The mouthpiece is also preferably sealed by means of a covering (not shown).

The parts can be packaged together as an article of manufacture, or kit. The parts can be contained within or separately packaged within a packaging material, such as a bag or a box. The kit may further include instructions for assembling the parts of the dry powder inhaler together and/or use of the dry powder inhaler. Such instructions can be in the form of a package insert, a label or a tag, or the like.

Thus, the invention has been described with reference to various specific and preferred embodiments and techniques. However, it should be understood that many variations and modifications may be made while remaining within the spirit and scope of the invention, and the invention is not to be construed as limited to the specific embodiments shown in the drawings.

What is claimed is:

1. A dry powder medication inhaler, comprising:

a tubular shell member having a first end and a second end with an air passageway therethrough, an air inlet aperture proximate the first end and an air outlet proximate the second end, and a chamber adapted for containing a dry powder medicament extending through the shell into the air passageway; the medicant-containing chamber having a first end and a second end, the first end of the chamber having an aperture sized for receiving the medicament and the second end of the chamber having an aperture sized for dispensing the medicament;

an axially moveable member which is affixed to the first end of the shell member, and functional to close the air inlet aperture;

a slidable dosing tray for dispensing the medicament from the medicament-containing chamber into the air passageway; the slidable dosing tray having a first end and a second end, the first end being affixed to the air inlet closure member and the second end including a member adapted to receive a metered dosage amount of the medicament from the dispensing aperture of the medicament-containing chamber;

a baffle positioned between the axially moveable member and the medicament-containing chamber, the baffle being configured to form an orifice sized to create a Venturi effect to cause suction of the medicament into the air flow therethrough;

wherein when the moveable air inlet closure member is moved axially from a closed position to an opened position to expose the air inlet aperture, the slidable dosing tray and the metering member containing the dosage amount of medicament are moved axially and upstream from the orifice, and the second end of the dosing tray seals the dispensing aperture of the storage tray;

and upon inhalation of air by a patient through the air outlet aperture, air flows through the air inlet aperture into the air passageway and mixes with the medicament in the metering member, and the air/medicament mixture passes through the orifice and through the air outlet aperture into the lungs of the patient.

2. The dry powder inhaler of claim 1, further comprising: a baffle member in the air passageway between the medicament-containing chamber and the air outlet aperture; the baffle member operable to provide air flow to prevent settling of particles of the medicament, to separate agglomerated particles of the medicament, to about evenly distribute particles of the medicament throughout the air flow, or a combination thereof.

3. The dry powder inhaler of claim 1, wherein the orifice is about 0.08–0.15 in$^2$.

4. The dry powder inhaler of claim 1, comprising multiple air inlet apertures.

5. The dry powder inhaler of claim 1, wherein the shell member further comprises means for viewing the medicament in the medicament-containing chamber.

6. The dry powder inhaler of claim 1, wherein the metering member is in the form of a depression that is sized to contain a dosage amount of medicament.

7. A method for treating a lung ailment of a patient, comprising: inhaling a medicament effective to treat the lung ailment using the dry powder inhaler of claim 1.

8. The method of claim 7, wherein the lung ailment is asthma, chronic obstructive lung disease, cystic fibrosis, or pneumonia.

9. The method of claim 7, wherein the medicament is selected from the group consisting of an aminoglycoside, mucolytic agent, peptide hormone, antiinflammatory steroid drug, and bronchodilator drug.

10. A method for treating a lung ailment of a patient, comprising:
 a) placing the mouth of a person over the air outlet aperture of the dry powder inhaler of claim 1; the inhaler containing a medicament effective to treat the lung ailment;
 b) axially moving the air inlet closure member from a closed position wherein the air inlet aperture is covered by the closure member, to an opened position wherein the air inlet aperture is exposed, whereupon the slidable dosing tray and the metering member containing the medicament are moved axially and upstream from the orifice, and the second end of the dosing tray seals the dispensing aperture of the storage tray;
 c) having the patient inhale to cause air to flow through the air inlet aperture into the air passageway and mix with the medicament in the metering member, whereupon the air/medicament mixture is dispensed into the lungs of the patient.

11. An article of manufacture, comprising: the dry powder inhaler of claim 1 packaged within containing means, and instruction means for using the inhaler for treating a lung ailment.

12. The article according to claim 11, wherein the instructions means is a label or tag attached to the packaging, a printed package insert, or a combination thereof.

13. An article of manufacture, comprising one or more separate components (a)-(d) of the dry powder inhaler of claim 1, packaged within containing means:
 (a) a tubular shell member having a first end and a second end with an air passageway therethrough, an air inlet aperture proximate the first end and an air outlet aperture proximate the second end, and a chamber adapted for containing a dry powder medicament extending through the shell into the air passageway; the medicament-containing chamber having a first end and a second end, the first end of the chamber having an aperture sized for receiving the medicament and the second end of the chamber having an aperture sized for dispensing the medicament;
 (b) an air inlet closure member that is axially moveable and capable of being affixed to the first end of the shell member, and functional to close the air inlet aperture;
 (c) a slidable dosing tray for dispensing the medicament from the medicament-containing chamber into the air passageway; the slidable dosing tray having a first end and a second end, the first end being capable of being affixed to the air inlet closure member and the second end including a metering member adapted to receive a metered dosage amount of the medicament from the dispensing aperture of the medicament-containing chamber; and
 (d) a baffle member capable of being affixed to an inner wall of the shell member between the axially moveable member and the medicament-containing chamber, the baffle being configured to form an orifice sized to create a Venturi effect to cause suction of the medicament from the metering member of the slidable dosing tray into the air flow therethrough.

14. The article according to claim 13, wherein the component (b) air inlet closure member is attached to the component (c) slidable dosage tray.

15. The article according to claim 13, further comprising a dry powder medication, instruction means for assembly of the inhaler, instruction means for use of the inhaler, or a combination thereof.

* * * * *